United States Patent [19]

Handley, III et al.

[11] Patent Number: 5,491,090
[45] Date of Patent: Feb. 13, 1996

[54] EMBRYOGENIC CONIFEROUS LIQUID SUSPENSION CULTURES

[75] Inventors: Levis W. Handley, III, Charleston, S.C.; Alice P. Godbey, Teaneck, N.J.

[73] Assignee: Westvaco Corporation, New York, N.Y.

[21] Appl. No.: 391,603

[22] Filed: Feb. 21, 1995

Related U.S. Application Data

[63] Continuation-in-part of Ser. No. 194,091, Feb. 9, 1994, abandoned.

[51] Int. Cl.$^6$ ................................ A01H 4/00; A01H 7/00
[52] U.S. Cl. ................................ 435/240.46; 435/240.49; 435/240.54
[58] Field of Search ................ 435/240.46, 240.49, 435/240.54

[56] References Cited

U.S. PATENT DOCUMENTS

| | | | |
|---|---|---|---|
| 5,034,326 | 7/1991 | Pullman et al. | 4354/240.4 |
| 5,036,007 | 7/1991 | Gupta et al. | 435/240.45 |
| 5,183,757 | 2/1993 | Roberts | 435/240.49 |
| 5,187,092 | 2/1993 | Uddin | 435/240.45 |
| 5,413,930 | 5/1995 | Becwar et al. | 435/240.49 |

OTHER PUBLICATIONS

Attree, S. M., M. K. Pomeroy, and L. C. Fowke. Manipulation of conditions for the culture of somatic embryos of white spruce for improved triacylglycerol biosynthesis and desiccation tolerance. *Planta* 187:395–404, 1992.

Attree, S. M., D. I. Dunstan, and L. C. Fowke. Initiation of embryogenic callus and suspension cultures, and improved regeneration from protoplasts, of white spruce (*Picea glauca*). *Canadian Journal of Botany* 67:1790–1795, 1989.

Attree, S. M., T. E. Tautorus, D. I. Dunstan, and L. C., Fowke. Somatic embryo maturation, germination, and soil establishment of plants of black and white spruce (*Picea mariana* and *Picea glauca*). *Canadian Journal of Botany* 68:2583–2589, 1990.

Becwar, M. R., R. Nagmani, and S. R. Wann. Initiation of embryogenic cultrues and somatic embryo development in loblolly pine (*Pinus taeda*). *Canadian Journal of Forest Research* 20:810–817, 1990.

Becwar, M. R., T. L. Noland, and S. R. Wann. A method for quantification of the level of somatic embryogenesis among Norway spruce callus lines. *Plant Cell Reports* 6:35–38, 1987.

Becwar, M. R., S. R. Wann, M. A. Johnson, S. A. Verhagen, R. P. Feirer, and R. Nagmani. Development and characterization of in vitro embryogenic systems in conifers. *Somatic Cell Genetics of Woody Plants* (pp. 1–18), 1988.

De Touchet, B., Y. Duval, and C. Pannetier. Plant regeneration from embryogenic suspension cultures of oil palm (*Elaeis quineensis* Jacq.) *Plant Cell Reports* 10:529–532, 1991.

Durzan, D. J. and P. K. Gupta. Somatic embryogenesis and polyembryogenesis in Douglas fir cell suspension cultures. *Plant Science* 52:229–235, 1987.

Ebert, A. and H. F. Taylor. Assessment of the changes of 2,4–dichlorophenoxyacetic acid concentrations in plant tissue culture media in the presence of activated charcoal. *Plant Cell Tissue and Organ Culture* 20:165–172, 1990.

Ebert, A., F. Taylor, and J. Blake. Changes of 6–benzylaminopurine and 2,4–dichloro–phenoxyacetic acid concentrations in plant tissue culture media in the presence of activated charcoal. *Plant Cell Tissue and Organ Culture* 33:157–162, 1993.

Finer, J. J., H. B. Kriebel, and M. R. Becwar. Initiation of embryogenic callus and suspension cultures of eastern white pine (*Pinus strobus L.*). *Plant Cell Reports* 8:203–206, 1989.

Grossnickle, S. C., D. R. Roberts, J. E. Major, R. S. Folk, F. B. Webster, and B. C. S. Sutton. Integration of somatic embryogenesis into operational forestry: Comparison of interior spruce emblings and seedlings during production of 1+0 stock. In: Proceedings, Intermountain Forest Nursery Association. Aug. 12–16, 1991. Park City, Utah. USDA Forest Service, General Tech. Report RM–211. pp. 106–113, 1992.

Gupta, P. K. and D. J. Durzan. Shoot multiplication from mature trees of Douglas–fir (*Pseudotsuga menziesii*) and sugar pine (*Pinus lambertiana*). *Plant Cell Reports* 4:177–179, 1985.

Gupta, P. K. and D. J. Durzan. Biotechnology of somatic polyembryogenesis and plantlet regeneration in loblolly pine. *Bio/Technology* 5:147–151, 1987a.

Gupta, P. K. and D. J. Durzan. Somatic embryos from protoplasts of loblolly pine proembryonal cells. *Bio/Technology* 5:710–712, 1987b.

Gupta, P. K., S. V. Kendurkar, V. M. Kulkarni, M. V. Shirgurkar, and A. F. Mascarenhas. Somatic embryogenesis and plants from zygotic embryos of coconut (*Cocos nucifera L.*) in vitro. *Plant Cell Reports* 3:222–225, 1984.

Gupta, P. K., G. S. Pullman, R. Timmis, M. E. Kreitinger, W. C. Carlson, and D. E. Welty. Scale–up somatic embryogenesis of conifers for reforestation (Abstract). In: Proceedings, 3rd Inter. Assoc. of Plant Tissue Culture Canadian Workshop on Plant Tissue Culture and Genetic Engineering, Univ. of Guelph, Guelph, Ontario, Canada. Jun. 17–20, 1992.

Hakman, I. and S. von Arnold. Plantlet regeneration through somatic embryogenesis in *Picea abies* (Norway spruce). *Journal of Plant Physiology* 121:149–158, 1985.

Hakman, I. C. and S. von Arnold, Somatic embryogenesis and plant regeneration from suspension cultures of *Picea glauca* (White spruce). *Physiologia Plantarum* 72:579–587, 1988.

(List continued on next page.)

*Primary Examiner*—David T. Fox
*Attorney, Agent, or Firm*—Daniel B. Reece, IV; Terry B. McDaniel; Richard L. Schmalz

[57] ABSTRACT

This invention relates to a method for regeneration of coniferous plants. In particular, this invention relates to an improved method for establishing and maintaining embryogenic liquid suspension cultures for use in somatic embryogenesis processes from plants of the genus Pinus and Pinus interspecies hybrids. This method is well suited for producing clonal planting stock useful for reforestation.

26 Claims, No Drawings

OTHER PUBLICATIONS

Hakman, I. and L. C. Fowke. An embryogenic cell suspension culture of *Picea glauca* (White spruce). *Plant Cell Reports* 6:20–22, 1987.

Hakman, I., L. C. Fowke, S. von Arnold, and T. Eriksson. The development of somatic embryos in tissue cultures initiated from immature embryos of *Picea abies* (Norway spruce). *Plant Science Letters* 38:53–59, 1985.

Jain, S. M., N. Dong, and R. J. Newton. Somatic embryogenesis in slash pine (*Pinus elliottii*) from immature embryos cultured in vitro. *Plant Science* 65:233–241, 1989.

Laine, E., P. Bade, and A. David. Recovery of plants from cryopreserved embryogenic cell suspensions of *Pinus caribaea*. *Plant Cell Reports* 11:295–298, 1992.

Laine, E. and A. David. Somatic embryogenesis in immature embryos and protoplasts of *Pinus caribaea*. *Plant Science* 69:215–224, 1990.

Michler, C. H., T. M. Voelker, and R. Moioffer. Effects of embryo explant type and development maturity on eastern white pine (Pinus strobus L.) embryogenic callus initiation (Abstract). In: Applications of biotechnology to tree culture, protection and utilization. (eds Haissig et al) Columbus, Ohio. Aug. 5–8, 1991. USDA Forest Serv., Northeastern Forest Experiment Station, p. 117, 1991.

Preston, R. J. North American Trees, 4th edition. Iowa State Univ. Press, Ames. pp. 4–7, 1989.

Roberts, D. R., B. S. Flinn, D. T. Webb, F. B. Webster, and B. C. Sutton. Abscisic acid and indole–3–butyric acid regulation of maturation and accumulation of storage proteins in somatic embryos of interior spruce. *Physiologia Plantarum;* 78:355–360, 1990.

Sharma, D. R., S. Deepak, and J. B. Chowdhury, Regeneration of plantlets from somatic tissues of the date palm *Phoenix dactylifera* Linn. *Indian Journal of Experimental Biology* 24:763–766, 1986.

Sutton, B. C. S., S. C. Grossnickle, D. R. Roberts, J. H. Russell, and G. K. Kiss. Somatic embryogenesis and tree improvement in interior spruce. *Journal of Forestry* 91:34–38, 1993.

Tautorus, T. E., S. M. Attree, L. C. Fowke, and D. I. Dustan. Somatic embryogenesis from immature and mature zygotic embryos, and embryo regeneration from protoplasts in black spruce (*Picea–mariana* Mill.). *Plant Science* 67:115–124, 1990.

Tautorus, T. E., L. C. Fowke, and D. I. Dunstan. Somatic embryogenesis in conifers. *Canadian Journal of Botany* 69:1873–1899, 1991.

Tautorus, T. E., M. M. Lulsdorf, S. I. Kikcio, and D. I. Dunstan. Bioreactor culture of *Picea mariana* Mill. (black spruce) and the species complex *Picea glauca–engelmannii* (interior spruce) somatic embryos. Growth parameters. *Applied Microbiology and Biotechnology* 38:46–51, 1992.

von Arnold, S. and I. Hakman. Regulation of somatic embryo development in *Picea abies* by abscisic acid (ABA). *Journal of Plant Physiology* 132:164–169, 1988.

Webster, F. B., D. R. Roberts, S. M. McInnis, and B. C. S. Sutton. Propagation of interior spruce by somatic embryogenesis. *Canadian Journal of Forest Research* 20:1759–1765, 1990.

EMBRYOGENIC CONIFEROUS LIQUID SUSPENSION CULTURES

This application is a continuation-in-part of our commonly assigned, U.S. patent application Ser. No. 08/194,091 filed Feb. 9, 1994, now abandoned, entitled "Embryogenic Coniferous Liquid Suspension Cultures."

FIELD OF INVENTION

This invention relates to a method for regeneration of coniferous plants. In particular, this invention relates to an improved method for establishing and maintaining embryogenic liquid suspension cultures for use in somatic embryogenesis processes for plants of the genus Pinus and Pinus interspecies hybrids. This method is well suited for producing clonal planting stock useful for reforestation.

BACKGROUND OF THE INVENTION

Reforestation, the controlled regeneration of forests, has become an integral part of forest management in order to secure a renewable and sustainable source of raw material for production of paper and other wood-related products. Forest trees can be regenerated by either sexual or asexual propagation. Sexual reproduction of seedlings for reforestation has traditionally been the most important means of propagation, especially with coniferous species. However, inherent biological and economic limitations on the use of sexual reproduction methods for large-scale seed production have caused considerable interest to develop in utilizing asexual methods to propagate conifers; especially economically important conifers of the genera Picea, Pinus, and Pseudotsuga.

One may avoid these biological limitations by using asexual propagation to exercise a very high selection intensity—that is, to propagate only progeny showing a very high genetic gain potential. As desirable progeny have genetic combinations which result in superior growth and performance characteristics, such progeny may be clonally propagated to develop a collection of genetically identical individuals for planting. Clone deployment has the capacity to increase fiber production and assure uniformity in field planting stocks.

The primary asexual propagation methods for trees are vegetative propagation (via either rooted stem cuttings or somatic embryogenesis) and grafting. Although grafting is widely used to propagate selected individuals in limited quantities for seed orchard establishment, it is not applicable to large-scale production for reforestation. Vegetative propagation via rooted stem cuttings or via somatic embryogenesis currently holds the most potential for reforestation of coniferous trees. Both methods contain benefits for forestry operations, depending upon the desired application.

Propagation by somatic embryogenesis refers to methods whereby embryos are produced in vitro from small pieces of plant tissue or individual cells. The embryos are referred to as somatic because they are derived from the somatic (vegetative) tissue, rather than from the sexual process. Vegetative propagation via somatic embryogenesis has the capability to capture all genetic gain of highly desirable genotypes. Furthermore, these methods are readily amenable to automation and mechanization. Thus somatic embryogenesis has the potential to produce large numbers of individual clones for reforestation.

It was not until 1985 that somatic embryogenesis was discovered in conifers (Hakman et al. 1985) and the first viable plantlets were regenerated from conifer somatic embryos (Hakman and von Arnold 1985). Since 1985, conifer tissue culture workers throughout the world have pursued the development of somatic embryogenesis systems capable of regenerating plants. The goal of much of this work is to develop conifer somatic embryogenesis as an efficient propagation system for producing clonal planting stock en masse. In addition, the embryogenic system interfaces very well with genetic engineering techniques for production of transgenic clonal planting stock of conifers.

The two most economically important conifer genera are Picea (spruce) and Pinus (pine). There are about 30 species of Picea, largely restricted to cooler regions of the northern hemisphere, of which seven species are native to North America. Pinus is the largest and most important genus of conifers, having approximately 95 species scattered over the northern hemisphere. Of these 95 species, 36 are native to North America (Preston 1989).

Those working in conifer somatic embryogenesis have found that there is a striking difference between Picea conifers and Pinus conifers as to the ease with which somatic embryogenesis can be induced and plants regenerated (Tautorus et al. 1991). Indeed, if one evaluates the success of somatic embryogenesis in conifers among species of these two important genera, it is clear that much more success has been achieved with Picea than with Pinus. It is also striking how consistent the success on developing somatic embryogenic systems has been among several Picea species, whereas the recalcitrance of Pinus has been equally consistent across several species.

Among Picea species embryogenic culture initiation frequencies are relatively high; as high as 95% from immature zygotic embryos and as high as 55% from mature zygotic embryos harvested from fully developed, dry seeds (Tautorus et al. 1991). There are numerous reports of production of fully developed somatic embryos among Picea species, and several reports of establishment and growth of Picea somatic embryo plants in soil. Researchers at the British Columbia Research Corporation have reported on establishment of interior spruce (a mixture of *Picea glauca* and *Picea englemannii*) somatic embryo plants under nursery conditions. For example, Webster et al. (1990) reported over 80% survival and establishment in nursery conditions of interior spruce somatic embryo plants for most of 71 genotypes tested. Grossnickle et al. (1992) reported the establishment of 40% of 2000 interior spruce somatic embryo plants in nursery conditions. The somatic embryo plants were derived from 15 different genotypes. Researchers at the Weyerhaeuser Company have reported similar success with Norway spruce (*Picea abies*); over 3000 somatic embryo plants from 17 genotypes have been established in the field (Gupta et al. 1992). Similar success was also reported with Douglas-fir (*Pseudotsuga menziesii*); over 2000 somatic embryo plants from 6 genotypes of have been established in soil in greenhouse conditions. Thus, conifer somatic embryogenesis workers utilizing Picea species (and commercially important Douglas-fir) have been successful in developing culture initiation, maintenance, and regeneration systems that enable relatively routine production of plants capable of transfer to field conditions. The rapid successes in Picea somatic embryogenesis had led to considerable optimism among researchers that commercial utilization of conifer somatic embryogenesis for production of clonal planting stock of Pinus conifers would be readily achievable.

However, the progress achieved with somatic embryogenesis in Pinus species to date has been much less encouraging than that achieved with Picea species. First and foremost in difficulty is the recalcitrance of Pinus species for initiation of embryogenic cultures. For example, initiation frequencies of about 1 to 5% are routinely cited by those working with Pinus species (Gupta and Durzan 1987a, Becwar et al. 1988, Jain et al. 1989, Becwar et al. 1990). The single report claiming a 54% initiation rate from immature zygotic embryos of *Pinus strobus* (Finer et al. 1989) has yet to be repeated or duplicated by others working with this species (Michler et al. 1991). Secondly, it is extremely difficult to obtain reliable development of Pinus somatic embryos to the fully developed (cotyledonary) stage. In addition, subsequent production of plantlets has been extremely limited in Pinus species. Tautorus et al. (1991) cited only 3 of 7 reports which indicated plantlets were obtained via somatic embryogenesis in Pinus species. (In contrast, 30 of 43 reports with Picea species reported obtaining plantlets via somatic embryogenesis.) Unlike the reports with Picea species where several systems have shown potential for plantlet production on relatively large scales, the reports of plantlet production from Pinus species have yielded few plants. To our knowledge there is only one report of successful establishment of Pinus somatic embryos in soil (Gupta and Durzan 1987a). The authors of this report have had limited success in obtaining *Pinus taeda* somatic embryo plants . . . indeed, only one culture genotype was taken to the plantlet stage and only one plant was transferred to soil (see Pullman and Gupta 1991). To date the only published report of higher numbers of germination of Pinus somatic embryos is for *Pinus caribaea*, where 34 of 69 (49%) germinated (Laine and David 1990). However, the authors did not report establishment of these plants in field conditions.

The recalcitrance seen in the initiation, development, and field establishment of somatic embryo plants in Pinus when compared to other conifers is also true for the establishment of Pinus embryogenic liquid suspension cultures. Shake flask suspension cultures have been established from embryogenic tissues in *Picea abies* (Hakman et al. 1985), *Picea glauca* (Hakman and Fowke 1987; Attree et al. 1989), *Pseudostuga manziesii* (Durzan and Gupta 1987), *Picea mariana* (Tautorus et al. 1990), and *Picea glauca-engelmannii* (Tautorus et al. 1992). In these species both the development of stage 3 embryos and recovery of complete plantlets have been accomplished (Hakman and von Arnold 1988; Attree et al. 1990), (Durzan and Gupta 1987; Tautorus et al. 1992). As has been the case with other tissue culture systems in conifers, both Picea and Pseudostuga have historically been much more amenable to the somatic embryogenesis process and, therefore, the establishment of embryogenic suspension cultures in Picea and Pseudostuga are generally considered routine.

However, the genus Pinus has been a much more recalcitrant species in both semi-solid and liquid tissue culture systems. Indeed, there are very few examples of the successful establishment of embryogenic liquid suspension cultures in Pinus—and in only two cases were stage 3 embryos developed from embryogenic liquid suspension cultures. To date, embryogenic suspensions have been reported in *Pinus taeda* (Gupta and Durzan 1987a and 1987b; Gupta and Pullman 1991; Pullman and Gupta 1991), *Pinus strobus* (Finer et al. 1989) and *Pinus caribaea* (Laine and David 1990; Laine et al. 1992).

Moreover, of these reports only in *Pinus caribaea* (Laine et al. 1992) have suspension cultures given rise to stage 3 embryos that were then germinated to plantlets and subsequently transferred to soil. These plants were obtained from suspension cultures that were either cryostored or non-cryostored and, apparently, these cultures were established from only one or two genotypes. There were no data given as to the actual numbers of stage 3 embryos produced. In contrast, the present method produced large numbers of stage 3 embryos from several different genetic lines. A major difference between this reported process and the present method is that the present method teaches the addition of activated carbon to suspension cultures, while the reported process does not.

In *Pinus taeda*, Gupta and Durzan (1987a and 1987b) report the development of somatic embryos from suspension cultures—however, apparently these were only globular or torpedo-shaped embryos (therefore presumably stage 1 and stage 2 embryos). No data were presented as to the numbers, if any, of late stage 3 embryos produced. Furthermore, the plantlets that were produced in this report (Gupta and Durzan 1987a) were from embryogenic tissues grown on a semi-solid medium, not from liquid cultures. Finally, in contrast to the present method the reported processes did not utilize activated carbon in suspension cultures.

In a recent patent Gupta and Pullman (1991) report on the development of embryos of *Pinus taeda* from a suspension culture using activated charcoal and abscisic acid (ABA) on a semi-solid development medium. These were apparently well developed stage 3 embryos, but were from two genotypes only (denoted as genotype A and genotype B). However, the reported process did not utilize activated carbon in its liquid suspension cultures.

Stage 3 embryos were produced In *Pinus strobus*, but no details were given as to either their morphology or their germination potential (Finer et al. 1989). Also, no data was given on the number of lines tried or on the efficiency of establishment and maintenance of the liquid culture system. This process also did not utilize activated carbon in the suspension culture medium.

Therefore, with the possible exception of *Pinus caribaea* no stage 3 somatic embryos capable of germination have been successfully produced in the genus Pinus from embryogenic liquid suspension cultures of a range of genotypes or cell lines. Moreover, while stage 3 embryos were produced in *Pinus caribaea*, the efficiency was extremely low (apparently only 2 plants were produced from 1 or 2 lines) and both plants showed phenotypic abnormalities (Laine et al. 1992).

Prior to the discovery of the present method it has been extremely difficult to establish viable suspension cultures from embryogenic tissue cultures of loblolly pine. For example, a series of experiments have shown that most embryogenic tissue cultures maintained on a semi-solid medium [containing DCR basal salts (Gupta and Durzan 1985 and Table I below) and vitamins with 3.0 mg/l 2,4-dichlorophenoxyacetic acid (2,4-D), 0.5 mg/l $N^6$-benzyladenine (BAP) and 2.0 g/l GELRITE® (gellan gum manufactured by Merck, Inc.)] would not grow when placed in a liquid medium of the same composition minus the gelling agent. Most cultures would not grow or would grow for a short time and die. In fact, out of 92 individual trials only 9 were successful and only 5 out of 18 different genetic lines were successfully maintained in a liquid environment.

Commonly assigned (and allowed) U.S. patent application Ser. No. 08/138,994, filed Oct. 21, 1993, now U.S. Pat. No. 5,413,930, which is hereby incorporated by reference, teaches and claims a process for regeneration of coniferous plants by somatic embryogenesis. The present method improves upon this process by allowing the practitioner to utilize liquid suspension cultures as embryogenic tissue maintenance media.

Therefore, an object of the present invention is to provide an improved method for establishing and maintaining embryogenic liquid suspension cultures for use in somatic embryogenesis processes for plants of the genus Pinus and Pinus interspecies hybrids.

Another object of the present invention is to provide an improved method for the regeneration of coniferous plants by somatic embryogenesis via the utilization of embryogenic liquid suspension cultures.

A further object of the present invention is to provide an improved method for the establishment and maintenance of embryogenic suspension cultures from plants of the genus Pinus and Pinus interspecies hybrids so that these cultures can be further induced to regenerate stage 3 embryos when placed in the development stage, and further germinated and converted to yield viable plants for field planting.

SUMMARY OF THE INVENTION

The above objectives are achieved by the use of an improved method for establishing and maintaining embryogenic suspension cultures for use in somatic embryogenesis processes employing embryogenic tissues from plants of the genus Pinus and Pinus interspecies hybrids. This method allows the practitioner to establish and maintain viable Pinus embryogenic cell cultures in a liquid medium. This was accomplished via the addition of activated carbon to the liquid culture medium in which the tissue culture cells are placed and grown. The activated carbon is utilized in combination with either standard (i.e., traditional levels used in plant tissue culture) or high levels of growth regulators in the liquid culture medium.

The use of liquid suspension cultures have certain inherent advantages over the use of semi-solid media cultures. For example, liquid suspension cultures are much less labor intensive to maintain than cultures grown on semi-solid media. Liquid suspension cultures also have the capacity to multiply large numbers of cells quickly and efficiently by the use of either shake flask cultures or bioreactors. A key component for automated somatic embryogenesis processes seeking to produce large numbers of individual clones for reforestation planting stock will be the capability to establish and maintain liquid suspension cultures of embryogenic cells. Employment of the present method will give the practitioner that capability.

DESCRIPTION OF THE PREFERRED EMBODIMENT

The present invention, an improved method for establishing and maintaining embryogenic suspension cultures for use in somatic embryogenesis processes employing embryogenic tissues from plants of the genus Pinus and Pinus interspecies hybrids, generally comprises the following sequential steps:

1. placing a suitable explant selected from the group consisting of immature zygotic embryos and megagametophytes containing immature zygotic embryos on culture initiation medium containing a sufficient amount of nutrients, 0.1 to 5.0 mg of auxin per liter of medium (mg/l), 0.1 to 1.0 mg/l of cytokinin, 5.0 to 100.0 g/l of a sugar selected from the group consisting of glucose, maltose, sucrose, melezitose, and combinations thereof, and a level of gelling agent selected from the group consisting of 2.5 to 4.5 g/l of agar, 0.5 to 1.5 g/l of gellan gum, 3.0 to 5.0 g/l of agarose, and 1.5 to 3.0 g/l of AGARGEL, for 2 to 14 weeks under suitable environmental conditions to grow a culture containing embryogenic tissue; and 2. transferring the embryogenic tissue culture to liquid suspension culture maintenance medium containing a sufficient amount of nutrients, 0.1 to 100.0 mg/l of auxin, 0.05 to 10.00 mg/l of cytokinin, 5.0 to 100.0 g/l of a sugar selected from the group consisting of glucose, maltose, sucrose, melezitose, and combinations thereof, and about 0.1 to 10.0 g/l of activated carbon, for a sufficient time under suitable environmental conditions to develop a liquid embryogenic cell culture.

This method of producing liquid suspension cultures may be incorporated and utilized in an improved method for producing coniferous plants via somatic embryogenesis. To do so, one follows these additional steps:

3. transferring about 30 mg of the liquid embryogenic cell culture to embryo development medium containing 5.0 to 250.0 mg/l of abscisic acid, a level of gelling agent selected from the group consisting of 6.0 to 12.0 g/l of agar, 1.75 to 4.00 g/l of gellan gum, 6.0 to 8.0 g/l of agarose, and 3.5 to 6.0 g/l of AGARGEL, and 20.0 to 70.0 g/l of a sugar selected from the group consisting of glucose, maltose, sucrose, and combinations thereof for a sufficient time under suitable environmental conditions to develop stage 3 somatic embryos;

4. separating the stage 3 somatic embryos from the development medium and partially drying the embryos by exposing the embryos to an atmosphere having a high relative humidity for sufficient time to permit the embryos to lose about 25% to 75% of their pre-dried weight;

5. transferring the partially dried somatic embryos to germination medium containing a sufficient amount of nutrients, up to 10.0 g/l of activated carbon, a level of gelling agent selected from the group consisting of 6.0 to 9.0 g/l of agar, 1.75 to 3.50 g/l of gellan gum, 6.0 to 8.0 g/l of agarose, and 3.5 to 5.0 g/l of AGARGEL, and 20.0 to 40.0 g/l of a sugar selected from the group consisting of glucose, maltose, sucrose, and combinations thereof for a sufficient time under suitable environmental conditions to germinate the partially dried embryos;

6. converting the germinated embryos into acclimatized plants; and 7. field planting the acclimatized plants.

Thus, somatic embryogenesis processes utilized with conifers (particularly the Pinus species) can be divided into seven general steps: 1) culture initiation, 2) culture maintenance, 3) embryo development, 4) embryo maturation, 5) embryo germination, 6) conversion, and 7) plant growth (field planting). An overview of these steps is given below:

1. Culture Initiation

In the culture initiation step explant material is collected from field-grown trees and placed into in vitro culture. This material is usually collected from immature seed cones, but could also be composed of mature seeds, mature needle tissue, or rejuvenated shoots. In loblolly pine (*Pinus taeda* L.), pitch by loblolly $F_1$ hybrids (*Pinus rigida*×*Pinus taeda*) and other Pinus species the only explant material that is responsive in the tissue culture process to date is immature seeds from immature seed cones. Thus, explants which are suitable for use in the present method may be selected from the group consisting of immature zygotic embryos and megagametophytes containing immature zygotic embryos. The seed cones are collected when the dominant zygotic embryo is in the precotyledonary stage of development or classified as stage 2 using the classification system of von Arnold and Hakman (1988). This stage usually occurs in mid to late July for *Pinus taeda* and in late June for *Pinus rigida×Pinus taeda* $F_1$ hybrid seed cones collected from breeding orchards in the Charleston, S.C. area. For culture initiation intact seeds are removed from seed cones, surface sterilized by treatment in a commercial bleach solution followed by sterile water rinses.

Once the seed surface is sterilized the seed coats of individual seeds are cracked open and the intact megagametophyte (which contains the developing zygotic embryos) is removed. The megagametophyte is placed on a semi-solid culture medium in petri dishes. Basal salt mixtures which have proven effective for culture initiation in Pinus include DCR basal salts formulation listed in Table I below (Gupta and Durzan 1985). The dishes are incubated in the dark at a constant temperature of 23° C. After about 7 to 21 days, embryogenic tissue extrudes from the micropyle of the megagametophyte explants. After about one month in culture, embryogenic tissue can be transferred to a new culture dish containing the same culture medium as used for initiation.

2. Culture Maintenance

Cultures are commonly maintained on semi-solid medium (usually the same medium as described for culture initiation) by subculturing masses of embryogenic tissue every 14 to 21 days to fresh medium. The environmental conditions for culture maintenance are the same as for culture initiation. Embryogenic tissues are normally subcultured by hand every three weeks by selecting the clear mucilaginous surface tissues off the individual tissue clumps and transferring these to new petri dishes containing fresh gelled medium. This is an extremely labor intensive process and requires many petri dishes to bulk up an individual culture line for large scale embryo development.

An alternative to maintaining cultures on solidified medium would be to maintain these in a liquid suspension medium. Heretofore, this has had very limited success in the genus Pinus and has been particularly difficult in loblolly pine (*Pinus taeda*). One advantage of using liquid medium is that cultures are much easier to maintain using this system. For example, many millions of somatic cells can be maintained in an individual flask and sub-cultured by simply pipetting cells from one flask into another flask of fresh medium.

Maintaining tissue cultures on semi-solid medium in petri dishes requires that embryogenic cells be carefully picked off each individual clump of tissue and then placed on a new petri dish containing fresh medium. This usually mandates the use of a microscope to subculture the tissues with the desired morphology, and can be a very tedious and time consuming process. When subculturing liquid suspensions the tedious hand labor and use of a microscope are eliminated.

Maintaining tissue cultures on semi-solid medium also requires the preparation of media containing some type of gelling agent such as agar, agarose or GELRITE. After autoclaving, the medium must be poured into each petri dish and allowed to gel. Once the medium gels the individual dishes must be repackaged and placed into some type of media storage facility. For large scale maintenance and production of many thousands of somatic embryos from many different genetic lines this would require large amounts of labor and storage space. With a liquid maintenance medium the preparation of media in many hundreds of petri dishes is eliminated. Additionally, very large quantities of a liquid medium can be prepared, frozen, and then stored in a freezer for extended periods of time. The medium can be thawed and used as needed. In contrast, GELRITE solidified media can not be frozen due to the disruption of the gel matrix which causes the gel to liquify when thawed. Thus, gel solidified medium can usually only be stored for only a limited time under ambient conditions before its effectiveness declines.

An additional benefit to using liquid suspensions in the maintenance step of the process is the ease with which cultures can be placed in the next step (the development phase of embryogenesis). When using tissue cultures on semi-solid medium this requires that petri dishes be unsealed and opened and embryogenic tissues transferred from the dishes containing maintenance medium to dishes containing development medium. Again this requires the use of a microscope and hand labor using forceps to pick off the best tissues from the maintenance dishes and place them on development medium. When using liquid suspension cultures, cells and medium can simply be pipetted from the shake flasks on to a support matrix, the liquid medium removed from the matrix, and the whole assembly placed on top of the development medium.

Finally, the paramount advantage to a liquid system is the ease with which it lends itself to automation. One can envision liquid culture bioreactors or "machines" where embryogenic cells could be routed through sterile tubing from one type of culture vessel to another without the involvement of any hand labor. A liquid culture system would be necessary for this type of system to be developed. Additionally, the liquid culture protocol in an automated system must also insure that the cells remain in an embryogenic state capable of producing large numbers of stage 3 embryos, capable of germination.

3. Embryo Development

At the end of a two to three week growth period on semisolid maintenance medium, small masses of embryogenic tissue (usually about 200 mg each) are transferred to a development medium containing the growth regulator ABA for a period of about 3 to 18 weeks. (The embryogenic tissue may be transferred onto a sterile permeable membrane which has been placed on the surface of the development medium if desired.) Basal salt mixtures which have proven effective for embryo development in Pinus include MSG basal salts formulation listed in Table I below (Becwar et al. 1990). As noted in Table II below, the MSG development medium contains maltose, a carbon source (Uddin 1993) and ABA, but does not contain activated carbon. About every 21 days the embryogenic tissues are transferred to fresh embryo development medium. Usually after two passages on the development medium cotyledonary somatic embryos (stage 3) are visible on the surface of the embryogenic tissue. Typically, multiple harvests of cotyledonary somatic embryos are made at the end of the second and third passage, and sometimes after the fourth passages on development medium.

The original culture from which the embryogenic tissue is derived is commonly maintained as stock culture on semisolid maintenance medium (as described in the maintenance step). However, the present process enables the practitioner to maintain such stock culture cells in a liquid medium. The present process also allows one to transfer these cells to other media via pipette, thereby eliminating the intensive hand manipulation and use of a microscope required when transferring cells from semisolid media. This significantly improves the ease in which cells from maintenance can be placed on development medium.

4. Embryo Maturation

Well developed stage 3 embryos in conifers can then be prepared for germination by a maturation drying treatment which reduces their water content and greatly enhances their ability to germinate. This system was first described in castor bean (Kermode and Bewley 1985) and in conifers has been effectively used in the spruces (Roberts 1993). This partial drying can be performed by incubating the embryos in multiwell culture dishes (Roberts et al. 1990b). After embryos are incubated in the drying treatment for about 21–28 days in the dark at 23° C. they are ready for germination.

5. Germination

Partially dried somatic embryos can be placed on the surface of a germination medium in sterile plastic petri dishes. The dishes containing the embryos are incubated in a growth chamber under lighted conditions. During germination the radicle (root) emerges and the epicotyl begins to grow.

6. Conversion and 7. Plant Growth

The term "conversion" includes the process of acclimatizing in vitro derived germinating somatic embryos in order for them to survive under ex vitro (nonaxenic) conditions, and continue to grow under ex vitro conditions. When the plantlets growing on germination medium reach sufficient size they can be aseptically removed from the dishes and planted in sterilized potting mix. Plants are usually transplanted into nursery containers in a soilless potting mix. Somatic embryo plants can be placed in a growth chamber or in a greenhouse mist chamber and incubated under high humidity conditions for plantlet growth and acclimation. Subsequently, somatic embryo plants can be transferred to ambient outdoor conditions. Acclimatized somatic embryo plants in containers can be transplanted to a field site for planting.

The present method specifically improves the second (maintenance) and third (development) stages of conifer somatic embryogenesis processes described above by enabling the establishment of liquid suspension cultures for the maintenance stage. Such suspension cultures are easier to manipulate and bulk-up in the maintenance step and, subsequently, easier to transfer into the development step. The method also permits the development of well formed stage 3 embryos having a high potential for normal germination and plant development from these liquid cultures. Heretofore, the establishment of routine and highly regenerable embryogenic liquid suspension culture systems for a variety of different genotypes of Pinus had not been possible.

To practice the present method one places suitable embryogenic tissues derived from plants of the genus Pinus or Pinus interspecies hybrids in a liquid suspension culture maintenance medium containing a sufficient amount of nutrients and plant growth regulators (auxin, cytokinin, etc.), and a level of activated carbon ranging from 0.1–5.0 g/l, for a sufficient time (usually 4–6 weeks) under suitable environmental conditions to establish a viable liquid embryogenic cell culture. One may subculture the embryogenic suspension cultures on a routine basis into the same liquid culture medium in order to maintain the cultures for an extended period of time. Such subculturing may also be accomplished by splitting or pipetting old cells and medium into new medium or by amending existing cultures with fresh medium.

The present method is also effective when the embryogenic tissues have been cryopreserved (and subsequently thawed) prior to being transferred to the liquid suspension culture maintenance medium. Likewise, the liquid embryogenic cell culture may also be cryopreserved for future use.

In practicing the present method, one would commonly grow the embryogenic tissues to be cultured in the liquid suspension maintenance medium via the procedure noted above (i.e., placing a suitable explant on culture initiation medium containing a sufficient amount of nutrients and plant growth hormones under suitable environmental conditions to produce the embryogenic tissues). However, any somatic embryogenic tissue capable of being maintained or established on a semi-solid culture medium is suitable for use in the present method.

This method is generally applicable to somatic tissue obtained from the Pinus species including, but not limited to, the following: *Pinus taeda* (loblolly pine), *P. elliottii* (slash pine), *P. palustris* (longleaf pine), *P. serotina* (pond pine), *P. echinata* (shortleaf pine), *P. clausa* (sand pine), *P. glabra* (spruce pine), *P. rigida* (pitch pine), *P. echinata* (shortleaf pine), *P. nigra* (Austrian pine), *P. resinosa* (red pine), *P. sylvestris* (Scotch pine), *P. banksiana* (jack pine), *P. virginiana* (Virginia pine), *P. radiata* (Monterey pine), *P. contorta* (shore pine), *P. contorta latifolia* (lodgepole pine), *P. ponderosa* (ponderosa pine), *P. leiophylla* (Chihuahua pine), *P. jeffreyi* (Jeffrey pine), and *P. engelmannii* (Apache pine), *P. strobus* (eastern white pine), *P. monticola* (western white pine), and *P. lambertiana* (sugar pine), *P. albicaulis* (whitebark pine), *P. flexilis* (limber pine), *P. strobiformis* (southwestern white pine), *P. caribaea* (Caribbean pine), *P. patula* (Mexican weeping pine), *P. tecumumanii* (Tecun Uman pine), *P. maximinoi*, *P. oocarpa* (Ocote Pine) and *P. chiapensis* (Mexican White pine). In addition, the current invention is specifically applicable to interspecies hybrids of the above mentioned pines including *Pinus rigida×P. taeda*, *P. serotina×P. taeda*, and reciprocal crosses.

It is preferred to utilize the present method with Southern yellow pines, *Pinus rigida*, and hybrids thereof. Those skilled in the art recognize that several species of pine indigenous to the Southeastern United States are closely related and hybridize naturally. Taxonomically this group of pines is referred to as "Southern yellow pines" and includes *Pinus taeda*, *P. serotina*, *P. palustris*, and *P. elliottii* (Preston 1989).

In addition to the taxonomically similarity of the above Southern yellow pine species, these species have also responded similarly studies on somatic embryogenesis attempts. For example, all previous reports of somatic embryogenesis with the above species have found the same stage, very early precotyledonary zygotic embryos, to be optimum for embryogenic culture initiation (see, e.g., Becwar et al., 1990, and Jain et al. 1989). Initiation frequencies were similarly low, about 1–5%, among these species. In all of the above reports the researchers were unsuccessful in obtaining somatic embryo development beyond the very early precotyledonary stage.

Both the culture initiation media and the liquid suspension culture maintenance media may contain from about 5.0 to 100.0 g/l of a sugar selected from the group consisting of glucose, maltose, sucrose, melezitose, and combinations thereof. The preferred sugar content in both of these media is from about 10.0 to 60.0 g/l.

The basic improvement contained in the present method lies in the incorporation of activated carbon into the liquid embryogenic cell culture medium. A suitable level of activated carbon for the present method is about 0.1–10.0 grams per liter of medium. The preferred level is about 0.5–5.0 g/l.

The activated carbon is utilized in combination with either standard (about 0.1 to 10.0 mg/l) or high (about 10.0 to 100.0 mg/l) levels of growth regulators in the liquid suspension culture maintenance medium. However, it is preferred to employ a standard level of growth regulators. The liquid suspension culture maintenance medium must contain from between 0.1–100.0 mg/l of auxin; with the preferred level being about 1.0–30.0 mg/l and the more preferred level being about 3.0–10.0 mg/l. Likewise, the liquid culture medium must also contain from between 0.05–10.00 mg/l of cytokinin; with the preferred level being about 0.1–5.0 mg/l and the more preferred level being about 0.5–3.0 mg/l.

Activated carbon has been used in various tissue culture media and is believed to be beneficial due to its ability to adsorb various phenolic or toxic compounds and/or due to its ability to adsorb excess levels of plant growth regulators. Activated carbon has also been used in various steps in the somatic embryogenesis process in conifers but not, to our knowledge, in liquid suspension cultures. Activated carbon has been used in a predevelopment medium in Norway spruce and loblolly pine (Becwar et al. 1987; Roberts et al. 1990a). In this case activated carbon is added to a semi-solid medium devoid of growth regulators for a short period of time (about one week), prior to placement on a development medium.

In two recent U.S. patents (U.S. Pat. Nos. 5,034,326 and 5,036,007) activated carbon with high levels of the growth regulator ABA has also been reported to be beneficial in the semi-solid development medium for various conifers. In this case activated carbon is added to a semi-solid medium containing the growth regulator ABA to stimulate the development of embryos. This fundamentally differs from the present method where activated carbon is employed in the maintenance step and not in the development step (that is, the opposite to what is taught in U.S. Pat. Nos. 5,034,326 and 5,036,007). Also, in the present method maintenance is in liquid medium, not on solid medium.

To our knowledge no one has tried using activated carbon in the liquid culture medium to establish liquid embryogenic cultures in conifers. There are reports in the literature where activated charcoal has been used in combination with auxin and cytokinins to initiate embryogenic callus on explants in coconut and date palm on semi-solid medium (Gupta et al 1984; Sharma et al. 1986). However, these were callus cultures on semi-solid medium, not suspension cultures. More importantly, in these systems the researchers routinely increased the concentration of the growth regulator auxin from 10 to 100 fold over levels generally used in plant tissue culture to compensate for the addition of the activated carbon in semi-solid or liquid medium. This is not necessary in the present method, as the growth regulator levels in this liquid system for pine can remain at the standard levels used for semi-solid culture systems even when activated carbon is added. In fact, it appears that keeping these levels low is beneficial to maintaining the cells in an embryogenic state.

There is only one report in palms on the use of activated carbon in a liquid suspension culture system (de Touchet et al. 1991). In this study on oil palm, as in the solid medium studies, the levels of 2,4-D employed ranged from 80–200 mg/l and the optimum levels were 80–100 mg/l. In palm embryogenic systems researchers have generally increased the levels of growth regulators when adding activated carbon to the semi-solid or liquid medium.

No prior art has been found where either standard (0.1–10.0 mg/l) or high (10.0–100.0 mg/l) levels of growth regulators coupled with activated carbon were used in the establishment and maintenance of an embryogenic liquid suspension culture system in conifers. Indeed, the literature teaches away from using standard levels of growth regulators in that activated carbon has been shown to readily adsorb auxins such as 2,4-D and cytokinins such as BAP in both semi-solid and liquid medium (Ebert and Taylor 1990; Ebert et al. 1993).

In addition to activated carbon and growth regulators, the suspension medium also requires sufficient amounts of nutrients to allow the culture to remain viable. However, the present method is not limited to any single culture nutrient medium formulation. For example, two common basal culture media formulations which were used in Examples 1–3 (designated DCR and MSG) are listed in Table I below. Although the listed basal media gave excellent results when employed in the present method, it should be understood that any nutrient media commonly used in Pinus somatic embryogenesis will be suitable for use with this invention.

TABLE I

Formulations Of Basal Culture Media

| COMPONENT | DCR[a] | MSG[b] |
|---|---|---|
| | CONCENTRATION, mg/l | |
| INORGANIC SALTS | | |
| $NH_4NO_3$ | 400.00 | — |
| $KNO_3$ | 340.00 | 100.00 |
| $Ca(NO_3)_2.4H_2O$ | 556.00 | — |
| $MgSO_4.7H_2O$ | 370.00 | 370.00 |
| $KH_2PO_4$ | 170.00 | 170.00 |
| $CaCl_2.2H_2O$ | 85.00 | 440.00 |
| KCl | — | 745.00 |
| KI | 0.83 | 0.83 |
| $H_3BO_3$ | 6.20 | 6.20 |
| $MnSO_4.H_2O$ | 22.30 | 16.90 |
| $ZnSO_4.7H_2O$ | 8.60 | 8.60 |
| $Na_2MoO_4.2H_2O$ | 0.25 | 0.25 |
| $CuSO_4.5H_2O$ | 0.25 | 0.03 |
| $CoCl_2.6H_2O$ | 0.03 | 0.03 |
| $NiCl_2.6H_2O$ | 0.03 | — |
| $FeSO_4.7H_2O$ | 27.80 | 27.80 |
| $Na_2EDTA$ | 37.30 | 37.30 |
| VITAMINS, AMINO ACID | | |
| Nicotinic acid | 0.50 | 0.50 |
| Pyridoxine.HCl | 0.50 | 0.10 |
| Thiamine.HCl | 1.00 | 0.10 |
| Glycine | 2.00 | — |

[a]According to Gupta and Durzan (1985)
[b]According to Becwar et al. (1990)

The conifer suspension cultures may be subcultured as desired (usually every 1–2 weeks). The volume of cells is measured and, when the volume has reached the desired level, new medium is added, the contents of the flasks are split, and new cultures are foiled. If a bioreactor-type system is used, fresh medium may be added to the existing culture.

Although the conifer suspension cultures may be grown in lighted conditions, it is preferred to grow them in the dark. A suitable temperature range for the cultures is 15°–30° C., with the preferred range being 20°–25° C. Suitable pH levels for the cultures depend in large part upon the type of basal culture medium formulation used. Commonly, the pH range is about 5–6.

To summarize, what is taught herein is an improved method for reproducing plants of the genus Pinus and Pinus interspecies hybrids by somatic embryogenesis; which comprises placing a suitable explant on culture initiation medium containing a sufficient amount of nutrients and plant growth hormones under suitable environmental conditions to grow embryogenic tissues, and subsequently transferring the embryogenic tissues to liquid suspension culture maintenance medium containing a sufficient amount of nutrients and plant growth hormones, and about 0.1– 5.0 grams of activated carbon per liter of medium, for a sufficient time under suitable environmental conditions to establish a liquid embryogenic cell culture. This method allows the liquid embryogenic culture cells to remain in an embryogenic state capable of producing large numbers of stage 3 embryos when transferred to a development medium with the capacity for subsequent germination. To achieve this, one may transfer about 30 mg (preferably about 100 mg) of liquid embryogenic culture cells to embryo development medium containing a sufficient amount of nutrients and plant growth hormones for a sufficient time under suitable environmental conditions to develop stage 3 somatic embryos. The stage 3 somatic embryos are subsequently separated from the development medium and partially dried for a sufficient period of time to permit the embryos to lose about 25– 75% of their pre-dried weight. The partially dried somatic embryos are then transferred to germination medium containing a sufficient amount of nutrients for a sufficient time under suitable environmental conditions to germinate the partially dried embryos. The germinated embryos may then be converted into acclimatized somatic embryo plants, and field planted.

A number of terms are known to have differing meanings when used in the literature. The following definitions are believed to be the ones most generally used in the field of botany and are consistent with the usage of the terms in the present specification.

A "bioreactor" is usually a large glass or stainless steel vessel where large quantities of living cells can be cultured in a liquid medium. Fresh medium is often supplied by continuous supply or by periodic enrichment.

A "cell line" is a culture that arises from an individual explant.

"Clone" when used in the context of plant propagation refers to a collection of individuals having the same genetic makeup.

"Corrosion cavity" is the cavity within the megagametophyte tissue of conifers formed by the growth and enlargement of the zygotic embryos.

"Conversion" refers to the acclimatization process that in vitro derived germinating somatic embryos undergo in order to survive under ex vitro (nonaxenic) conditions, and subsequent continued growth under ex vitro conditions.

An "embryogenic culture" is a plant cell or tissue culture capable of forming somatic embryos and regenerating plants via somatic embryogenesis.

"Embryogenic tissue" in conifers, is a mass of tissue and cells comprised of very early stage somatic embryos and suspensor-like cells embedded in a mucilaginous matrix. The level of differentiation may vary significantly among embryogenic conifer cultures. In some cases, rather than containing well-formed somatic embryos, the embryogenic tissue may contain small, dense clusters of cells capable of forming somatic embryos. This has also been referred to as "embryogenic suspensor masses" by some researchers and is also called "embryogenic callus" in some of the conifer somatic embryogenesis literature; but most researchers believe it is not a true callus.

"Epicotyl" is the first newly formed shoot to develop and grow above the seed leaves (cotyledons).

An "established" embryogenic liquid suspension culture is considered to be any culture that grows and can be maintained in a viable embryogenic state.

An "explant" is the organ, tissue, or cells derived from a plant and cultured in vitro for the purpose of starting a plant cell or tissue culture.

"Extrusion" is the process by which zygotic embryos and/or embryogenic tissue derived from zygotic embryos emerges or extrudes from the corrosion cavity of the megagametophyte of conifer seeds via the opening in the micropylar end, when placed in culture.

"Field planting" is the establishment of laboratory, greenhouse, nursery, or similarly grown planting stock under field conditions.

"Genotype" is the genetic constitution of an organism; the sum total of the genetic information contained in the chromosomes of an organism.

"Germination" is the emergence of the radicle or root from the embryo.

"Hypocotyl" is the section of the first newly formed shoot of an embryo above the radicle (root) and below the cotyledons.

"Initiation" is the initial cellular proliferation or morphogenic development that eventually results in the establishment of a culture from an explant.

"Megagametophyte" is haploid nutritive tissue of the conifer seed, of maternal origin, within which the conifer zygotic embryos develop.

"Micropyle" is the small opening in the end of the conifer seed where the pollen tube enters the ovule during fertilization, and where embryogenic tissue extrudes from the megagametophyte during culture initiation.

"Nutrients" are the inorganics (e.g., nitrogen), vitamins, organic supplements, and carbon sources necessary for the nourishment of the culture.

A "plantlet" is a small germinating plant derived from a somatic embryo.

"Regeneration" in plant tissue culture, is a morphogenic response to a stimuli that results in the production of organs, embryos, or whole plants.

"Stage 1 embryos" are small embryos consisting of an embryonic region of small, densely cytoplasmic cells subtended by a suspensor comprised of long and highly vacuolated cells.

"Stage 2 embryos" are embryos with a prominent (bullet shaped) embryonic region that is more opaque and with a more smooth and glossy surface than stage 1 embryos.

"Stage 3 embryos" are embryos with an elongated embryonic region with small cotyledons visible.

"Somatic embryogenesis" is the process of initiation and development of embryos in vitro from somatic cells and tissues.

A "somatic embryo" is an embryo formed in vitro from vegetative (somatic) cells by mitotic division of cells. Early stage somatic embryos are morphologically similar to immature zygotic embryos; a region of small embryonal cells subtended by elongated suspensor cells. The embryonal cells develop into the mature somatic embryo.

A "suspension culture" is a culture composed of cells suspended in a liquid medium, usually agitated on a gyrotory shaker. An embryogenic suspension culture in conifers is usually composed of early stage somatic embryos with well formed suspensor cells and dense cytoplasmic head cells that float freely in the liquid medium.

A "suspensor cell" is an extension of the base of the embryo that physically pushes the embryo into the megagametophyte in conifer seeds and is comprised of elongated and highly vacuolated cells. In a somatic embryo these elongated cells are cluster in rows and extend from the base of the dense cytoplasmic cells at the head or apex.

A "zygotic embryo" is an embryo derived from the sexual fusion of gametic cells.

The following examples are provided to further illustrate the present invention and are not to be construed as limiting the invention in any manner.

EXAMPLE 1

Immature seed cones were collected from several different loblolly pine (*Pinus taeda* L.) sources located in Westvaco's South Carolina coastal breeding orchards near Charleston, S.C. The seed cones were collected when the dominant zygotic embryo was at the precotyledonary stage of development. Using the classification system of von Arnold and Hakman (1988), the dominant zygotic embryo at this stage is referred to as being at stage 2; that is, an embryo with a prominent embryonic region with a smooth and glossy surface, subtended by elongated suspensor cells which are highly vacuolated. However, zygotic embryos at an earlier stage of development (stage 1) may also be used effectively to initiate embryogenic cultures.

Seed cones were harvested from selected trees, placed in plastic bags and stored at 4° C. until used for culture initiation. If the cones were stored for more than two weeks at 4° C., they were aired and dried out weekly (placed at 23° C., ambient laboratory conditions for 2–3 hours) to prevent growth of fungi on the surface of the cones and concomitant deterioration of seed quality.

For culture initiation intact seeds removed from seed cones were surface sterilized by treatment in a 10 to 20% commercial bleach solution (equivalent of a 0.525% to 1,050% sodium hypochlorite solution) for 15 minutes followed by three sterile water rinses (each of five minutes duration). Seeds were continuously stirred during the sterilization and rinsing process.

Megagametophytes containing developing zygotic embryos were used as the explant for culture initiation. The seed coats of individual seeds were cracked open under a laminar-flow hood with the use of a sterile hemostat. The intact megagametophyte (which contains the developing zygotic embryos) was removed from the opened seed coat with forceps. Tissues attached to the megagametophyte, such as the megagametophyte membrane and the nucellus, were removed from the megagametophyte and discarded. The megagametophyte was placed on culture medium (longitudinal axis of megagametophyte parallel to the surface of culture medium) with forceps. The micropyle end of the megagametophyte was placed in contact with (but not submerged in) the culture medium (see Table I, DCR).

Basal salt mixtures which have proven effective for culture initiation include the DCR basal salts formulation listed in Table I. (The complete formulations of the DCR medium used in the Examples are listed in Table II.). The pH of the medium was adjusted to 5.8 with KOH and HCl prior to autoclaving at 110 kPa (16 psi) and 121° C. for 20 minutes. Aqueous stock solutions of L-glutamine were filter sterilized and added to warm (about 60° C.) medium prior to pouring the medium into culture dishes. Approximately 20 ml of medium was poured into 100×15 mm sterile plastic petri dishes. For liquid culture media no gelling agent was added and the medium was stored in 500 ml batches under refrigeration or frozen prior to use.

The basal media modified for each of the culture stages are shown in Table II.

TABLE II

Composition Of Media Commonly Used In The Examples Below

| COMPONENT | Semi-Solid Initiation/Maintenance Medium DCR$_1$ | Liquid Maintenance Medium DCR$_2$ | Semi-Solid Development Medium MSG$_1$ | Semi-Solid Germination Medium MSG$_G$ |
|---|---|---|---|---|
| Basal medium[a] | DCR | DCR | MSG | MSG |
| CONCENTRATION (g/l) | | | | |
| Ammonium nitrate | — | — | — | 0.80 |
| Inositol | 0.50 | 0.50 | 0.10 | 0.10 |
| Casein hydrolysate | 0.50 | 0.50 | — | — |
| L-glutamine | 0.25 | 0.25 | 1.45 | — |
| Sucrose | 30.00 | 30.00 | — | 30.00 |
| Maltose | — | — | 60.00 | — |
| GELRITE | 1.00–2.00 | — | 2.00 | 2.00 |
| Activated carbon | — | 0.10–5.00 | — | 5.00 |
| CONCENTRATION (mg/l) | | | | |
| Auxin[b] | 3.00 | 1.00–30.00 | — | — |
| Cytokinin[c] | 0.50 | 0.05–5.00 | — | — |
| ABA[d] | — | — | 20.0–250.0 | — |

[a] Refer to Table I for composition of basal medium.
[b] 2,4-dichlorophenoxyacetic acid (2,4-D).
[c] N$^6$-benzylaminopurine [or N$^6$-benzyladenine (BAP)].
[d] Abscisic acid After megagametophyte explants were placed in culture, the perimeter of the dish was sealed with two wraps of PARAFILM® (manufactured by American Can Co.). The dishes were incubated in the dark at a constant temperature of 23° C. After about 7 to 21 days, embryogenic tissue extruded from the micropyle of the megagametophyte explants. After 28 days in culture embryogenic tissue was removed from responsive megagametophyte explants and moved to a new position on the same culture dish, or the embryogenic tissue was transferred to a new culture dish containing the same culture medium as used for initiation. Each individual culture derived from an individual megagametophyte explant was kept separate and assigned a cell line identification code.

Embryogenic tissue cultures were initiated and maintained on semi-solid DCR$_1$ medium containing 3.0 mg/l of 2,4-D, 0.5 mg/l of BAP, and 0.2% of GELRITE. The cultures were subcultured at three-week intervals by plating the newly formed, mucilaginous tissue on to fresh medium. In this Example attempts were made to establish suspension cultures by inoculating a 125 ml Nephelo sidearm flask (manufactured by Kontes Chemistry and Life Sciences Products) with 500 mg of these tissues.

Fifteen genetically different tissue culture lines were placed into two different liquid DCR$_2$ media with 30 mg/l 2,4-D, 5 mg/l BAP, and 2.5 g/l activated carbon; or in DCR$_2$ medium with 3 mg/l 2,4-D, 0.5 mg/l 2,4-D and no activated carbon using the above procedure. The two different liquid DCR media were prepared and poured into 125 ml Nephelo erlenmeyer flasks equipped with a sidearm. Suspension cultures were initiated by placing 10 mls liquid medium per flask. (For the complete medium formulations see Tables I and II above.) The flasks containing the cells in liquid medium were then placed on a gyrotory shaker at 100 rpm in a dark culture room at a temperature of 23°±1° C. One day following placement in the liquid medium, cells and medium were decanted into the sidearm portion of the flasks and allowed to settle for 30 minutes, after which time the settled cell volume (SCV) was recorded in millimeters for each flask by placing a ruler next to the sidearm. This measurement was made one day after initiation in order to allow air bubbles in the tissue clumps to disperse to enable the tissues to settle. At 7-day intervals the cell growth was measured in the sidearm by allowing the cells to settle for 30 minutes and then measuring the settled cell volume (SCV). When the SCV doubled from the original starting SCV, the liquid in each flask was brought up to 20 mls with fresh medium. When the SCV doubled again a flask was split 1:1 with a 125 ml non sidearm flask containing 20 mls fresh medium. This subculturing method, termed splitting, involved pouring 20 mls of fresh medium into the old culture flask, swirling to evenly distribute the cells, and pipetting 20 mls of the resulting 40-ml culture into a non-sidearm flask. At each 7-day interval the SCV was determined and the flasks were split when the SCV was greater than or equal to twice the starting SCV. After about 2 weeks the cultures in the medium containing activated carbon began to show obvious signs of growth and in about 4–6 weeks the cultures stabilized to the point where they needed to be subcultured every 7 to 14 days. While the cultures could be maintained in 20 mls in 125 ml sidearm flasks, they were instead transferred to 250 ml sidearm flasks containing 40 mls of medium for routine maintenance. When the SCV doubled in the 125 ml sidearm, the entire contents of the 125 ml flask were transferred to a 250 ml sidearm and an additional 20 mls of fresh medium was added to give a total volume of 40 mls of medium. At each 7-day interval, when the cultures doubled in volume they were split with a non-sidearm 250 ml flask with 40 mls of medium. The cells in the non-sidearm flask were used for development experiments or other studies.

In this study 14 of the 15 lines were successfully established using the medium containing activated carbon, whereas no lines were successfully established and grown in the medium without activated carbon. The 14 established lines were maintained in culture in 250 ml sidearm flasks for 34–47 weeks (8–11 months). All of them showed the typical loblolly pine embryogenic cell culture morphology with long suspensor-like cells appending dense cytoplasmic head-type cells. This is the first instance where as many as fourteen genetically different embryogenic tissue culture lines of Pinus were successfully established and maintained in a liquid culture medium.

After 3–8 months in culture each of these 14 lines was plated on GELRITE-solidified $MSG_1$ development medium containing from 20 to 250 mg/l ABA to assess the ability of the cultures to develop high quality harvestable stage 3 embryos. A sterile 90 mm sterile NITEX nylon membrane disk (#3-35/16XX, commercially available from Tetko, Inc.) was placed in a sterile Buchner funnel. Three 40 mm nylon disks were placed on top of this larger nylon disk in the funnel equidistant from one another but not touching. One ml of suspension culture cells and medium were pipetted onto each of the 40 mm disks. The liquid medium was suctioned from the cells using a mild vacuum. Each 40 mm nylon disk with cells was removed from the Buchner funnel and placed on GELRITE solidified $MSG_1$ development medium (see Table II) in 100× 25 mm plastic petri dishes. Dishes were incubated in a dark growth chamber at 23° C. The nylon disks were then transferred to new petri dishes containing fresh medium every 3 weeks.

At weeks 6, 9 and 12, stage 3 embryos were counted and those deemed suitable for germination were harvested. After 12 weeks on development medium all of the 14 lines developed stage 2 somatic embryos, and in six lines these developed further into stage 3 somatic embryos (which were subsequently harvested). While satisfactory results were obtained in that the development of these embryos indicated that these lines had maintained their embryogenic potential, the numbers of stage 3 embryos were somewhat low when compared to the embryo production from their semi-solid-grown tissue culture counterparts placed on the same development medium. This led to the conclusion that the cultural manipulations using the high levels of growth regulators along with activated carbon were somehow altering the embryogenic capacity of the cells in the liquid culture. This conclusion was tested in Example 2 below.

EXAMPLE 2

Following the procedures taught in Example 1 above, embryogenic tissue cultures from five loblolly pine sources were initiated on semi-solid $DCR_1$ medium with 3.0 mg/l 2,4-D, 0.5 mg/l BAP, and 0.1% GELRITE, and maintained on semi-solid $DCR_1$ medium with 3.0 mg/l 2,4-D, 0.5 mg/l BAP, and 0.2% GELRITE. The cultures were subsequently subcultured at three-week intervals by plating the newly formed, mucilaginous tissue on to fresh medium. In this Example attempts were made to establish suspension cultures by inoculating a 125 ml Nephelo sidearm flask with 500 mg of these tissues also using the procedures described in Example 1 above. Liquid $DCR_2$ media were prepared containing different levels of 2,4-D, BAP, and activated carbon in 125 ml Nephelo erlenmeyer flasks equipped with a sidearm. Suspension cultures were initiated by placing 10 mls medium/flask. The amount was increased up to 20 mls when the SCV doubled in volume. After the SCV doubled again suspensions were transferred to 250 ml sidearm flasks containing 40 mls of medium. Thereafter cultures were subculturing by splitting 1:1 with fresh medium when the SCV doubled.

The twenty media treatments (A through T) tested in this experiment are listed in Table III.

TABLE III

| Media Formulations Tested For Suspension Culture Establishment | | | | | |
|---|---|---|---|---|---|
| 2,4-D | BAP | Activated carbon g/l[1] | | | |
| mg/l[1] | mg/l[1] | 0.0 | 0.5 | 1.0 | 1.5 | 2.5 |
| 0.0 | 0.0 | A[2] | B | C | D | E |
| 3.0 | 0.5 | F | G | H | I | J |
| 10.0 | 2.0 | K | L | M | N | O |
| 30.0 | 5.0 | P | Q | R | S | T |

[1] All media formulations are in milligrams or grams of additive per liter of medium.
[2] Each letter represents the medium code for each particular additive combination.

The liquid maintenance part of this study was conducted for a total of 14 weeks. After that time the media in which suspension cultures had been successfully established were determined (and the results listed in Table IV below). Any culture that grew and was maintained by splitting was considered to be established.

TABLE IV

Number Of Successfully Established Cultures

| 2,4-D mg/l | BAP mg/l | NUMBER OF SUCCESSFUL CULTURES (OUT OF 5 LINES) ACTIVATED CARBON g/l[1] | | | | |
|---|---|---|---|---|---|---|
| | | 0.0 | 0.5 | 1.0 | 1.5 | 2.5 |
| 0.0 | 0.0 | 0[2] A | 1 B | 2 C | 1 D | 2 E |
| 3.0 | 0.5 | 1 F | 4 G | 4 H | 5 I | 4 J |
| 10.0 | 2.0 | 0 K | 3 L | 5 M | 5 N | 5 O |
| 30.0 | 5.0 | 0 P | 0 Q | 2 R | 2 S | 4 T |

[1] All media formulations are in milligrams or grams of additive per liter of medium.
[2] Each number represents the number of lines that were successfully established out of the five attempted. Each letter represents the medium code from Table III above.

We found that the addition of activated carbon to the liquid medium was highly beneficial in successfully establishing liquid cultures of embryogenic tissues from all five lines. Only one line was successfully established in a medium without activated carbon in the medium (medium F). The treatments that were the most prolific, as indicated by the average number of subcultures recorded during the 14-week culture period (see Table V), were those containing activated carbon with either 3 mg/l 2,4-D/0.5 mg/l BAP or 10 mg/l 2,4-D/2 mg/l BAP in combination with all levels of activated carbon (i.e. treatments G, H, I, J, L, M, N, O from TABLE III).

TABLE V

Subculture Data For The Number Of Times Each Flask Was Subcultured Over A 14-Week Period

| LINE[1] | NUMBER OF SUBCULTURES PER TREATMENT PER LINE | | | | | | | | | | | | | | | | | | |
|---|---|---|---|---|---|---|---|---|---|---|---|---|---|---|---|---|---|---|---|
| | A[2] | B | C | D | E | F | G | H | I | J | K | L | M | N | O | P | Q | R | S | T |
| 1 | 0 | 0 | 0 | 0 | 0 | 0 | 4 | 4 | 1 | 3 | 0 | 5 | 6 | 4 | 3 | 0 | 0 | 2 | 1 | 3 |
| 2 | 3 | 3 | 6 | 4 | 4 | 2 | 5 | 8 | 6 | 7 | 0 | 8 | 5 | 5 | 6 | 0 | 0 | 6 | 5 | 5 |
| 3 | 1 | 2 | 6 | 3 | 6 | 2 | 8 | 9 | 6 | 5 | 1 | 7 | 10 | 9 | 8 | 0 | 1 | 4 | 8 | 6 |
| 4 | 1 | 2 | 3 | 3 | 3 | 3 | 4 | 5 | 10 | 5 | 0 | 4 | 8 | 9 | 9 | 0 | 0 | 3 | 8 | 7 |
| 5 | 1 | 6 | 3 | 7 | 5 | 7 | 5 | 4 | 7 | 8 | 0 | 4 | 9 | 7 | 5 | 0 | 0 | 3 | 4 | 4 |
| Avg. Subs[3] | 1.2 | 2.6 | 3.6 | 3.4 | 3.6 | 2.8 | 5.2 | 6 | 6 | 7.6 | 0.2 | 5.6 | 7.6 | 6.8 | 6.2 | 0 | 0.2 | 3.6 | 5.2 | 5 |

[1] Each genetic line tested is labeled 1–5.
[2] Each letter represents the medium code from Table III above.
[3] Numbers in treatment blocks represent the average number of subcultures in a 14-week period.

The successful establishment of embryogenic suspension cultures using standard levels of growth regulators in combination with activated carbon is an unexpected result. Heretofore, most researchers have found or assumed it is necessary to increase the concentration of growth regulators in the culture medium to compensate for adsorption by activated carbon. However, this is not the case. As the results clearly show, a standard level of growth regulators (approximately 3 mg/l 2,4-D and 0.5 mg/l BAP) allowed for successful culture establishment and maintenance as long as activated carbon was present.

The liquid cultures from treatments F, G, H, I, J, L, M, N and O were pipetted onto GELRITE-solidified MSG$_1$ development medium containing rates of ABA varying from 21 to 250 mg/l using the nylon disk method shown in Example 1. There were six development dishes containing six different levels of ABA, prepared from each line. Three mls of suspension culture cells were pipetted onto 3 nylon disks on each dish (i.e. 1 ml was pipetted per disk). The nylon disks containing cells on top were subcultured at three week intervals. Stage 3 embryos were harvested from each nylon disk at the sixth, ninth and twelfth week of culture on development medium. The results of these studies are detailed in Table VI.

TABLE VI

Harvest Of Stage 3 Embryos Produced On Development Medium Containing Varying Rates Of ABA

| Original suspension medium treatment (see Table III)* | Stage 3 embryos harvested (Total number) |
|---|---|
| F | 87 |
| G | 133 |
| H | 350 |
| I | 222 |
| J | 195 |
| L | 201 |
| M | 246 |
| N | 101 |
| O | 58 |

*Letters refer to the original liquid medium tested (See Table III). Note: treatment F contained development dishes from 1 line as only 1 line was successfully established. Treatment L contained dishes from 3 lines. Treatments G, H and J contained dishes from 4 lines, and treatments I, M, N and O contained dishes from 5 lines.

Each suspension medium treatment containing the activated carbon with varying rates of growth regulators produced well-formed stage 3 somatic embryos showing excellent cotyledon and hypocotyl development. Only those embryos deemed capable of germination (based on studies on semi-solid culture development studies) were harvested. Therefore not only could liquid suspension cultures be successfully established but these cultures continued to be capable of producing large numbers of normal stage 3 somatic embryos when plated out on semi-solid development medium. The liquid media that contained activated carbon allowed more lines to be established and more embryos to be produced than the media without activated carbon.

EXAMPLE 3

Embryogenic tissue cultures were initiated following the method taught in Example 1 above. These tissue cultures were maintained on semi-solid DCR$_1$ medium with 3.0 mg/l 2,4-D, 0.5 mg/l BAP, and 0.2% gelrite and subcultured at three-week intervals by plating the newly formed, mucilaginous tissue on to fresh medium. In this study attempts were made to establish suspension cultures of 13 genetically different lines by inoculating a 125 ml Nephelo sidearm flask with 500 mg of these tissues using the procedures described in Example 1 above. Seven of the lines were derived from *Pinus taeda* and six were from the interspecies hybrid *Pinus rigida*×*P. taeda*. Liquid DCR$_2$ media were prepared containing 3.0 mg/l 2,4-D and 0.5 mg/l BAP with either 0, 0.5 or 1.0 g/l activated carbon in 125 ml Nephelo erlenmeyer flasks equipped with a sidearm. Tissues used to initiate the suspension cultures were placed in flasks containing 10 mls of medium. The medium volume was increased to 20 mls when the SCV doubled. After the SCV doubled again suspensions were transferred to 250 ml sidearm flasks containing 40 mls of medium. Thereafter when the SCV reached a volume of 11 mls or higher, cultures were subcultured by adding fresh medium and splitting to maintain a starting SCV of 5 mls at each subculture.

The media treatments tested in this experiment were media F, G and H listed in Table III. The liquid establishment and maintenance phases were conducted for a total of 9 weeks. After that time the media in which suspension cultures had been successfully established were determined (and the results listed in Table VII below). Any culture that grew and was maintained by splitting was considered to be established.

We again found that the addition of activated carbon to the liquid medium was highly beneficial in successfully establishing liquid cultures of embryogenic tissues. Six of the lines grew enough to be subcultured once in the medium without activated carbon (medium F) but did not continue to proliferate. The two treatments that grew and continued to grow prolifically, as indicated by those that were subcultured throughout the 9-week culture period (see Table VII), were those containing activated carbon with 3 mg/l 2,4-D and 0.5 mg/l BAP in combination with 0.5 or 1.0 g/l activated carbon (i.e. treatments G and H). The average subculture data show in Table VII that the cultures in each medium containing activated carbon were subcultured about every other week. However, the cultures in medium without activated carbon were subcultured only one time (at most) before the cultures expired. The results clearly indicated that a number of genetically different lines from both *Pinus taeda* and the interspecies hybrid *Pinus rigida*×*P. taeda* would respond to the treatments containing activated carbon. This again demonstrates that a standard level of growth regulators when combined with activated carbon is useful for the successful establishment of an actively growing embryogenic suspension culture of Pinus and Pinus hybrids.

TABLE VII

Subculture Data For The Number Of Times Each Flask Was Subcultured Over A 9-week Period

| LINE | NUMBER OF SUBCULTURES PER TREATMENT PER LINE | | |
|---|---|---|---|
| | F | G | H |
| LOB 1 | 0 | 2 | 4 |
| LOB 2 | 1 | 5 | 5 |
| LOB 3 | 1 | 6 | 5 |
| LOB 4 | 0 | 5 | 5 |
| LOB 5 | 0 | 3 | 4 |
| LOB 6 | 1 | 1 | 2 |
| LOB 7 | 0 | 1 | 2 |
| PXLOB 1 | 0 | 4 | 2 |
| PXLOB 2 | 0 | 5 | 4 |
| PXLOB 3 | 1 | 3 | 2 |
| PXLOB 4 | 0 | 6 | 7 |

TABLE VII-continued

Subculture Data For The Number Of Times Each Flask Was Subcultured Over A 9-week Period

| LINE | NUMBER OF SUBCULTURES PER TREATMENT PER LINE | | |
|---|---|---|---|
| | F | G | H |
| PXLOB 5 | 1 | 7 | 7 |
| PXLOB 6 | 1 | 6 | 5 |
| AVG. SUBS | 0.54 | 4.15 | 4.15 |

The liquid cultures from treatments G and H (the only two that grew) were pipetted onto GELRITE-solidified MSG$_1$ development medium containing a rate of ABA at 125 mg/l using the nylon disk method shown in Example 1. There were two development dishes prepared from each line. Three mls of suspension culture cells were pipetted onto 3 nylon disks on each dish (i.e. 1 ml was pipetted per disk). The nylon disks containing cells on top were subcultured to fresh medium at three week intervals. Stage 3 embryos were harvested from each nylon disk at the sixth, ninth and twelfth week of culture on development medium. The results of these studies are detailed in Table VIII. As the data in the table show, the cell cultures grown in the liquid culture media containing activated carbon produced a large number of somatic embryos.

TABLE VIII

Harvest Of Stage 3 Embryos Produced From Cells Plated On MSG Development Medium From 2 Different Suspension Culture Media

| Suspension culture line | Stage 3 embryos from original suspension medium treatment G* | Stage 3 embryos from original suspension medium treatment H* | Grand total Stage 3 embryos harvested (Total number) |
|---|---|---|---|
| LOB 1 | 93 | 38 | 131 |
| LOB 2 | 0 | 0 | 0 |
| LOB 3 | 24 | 0 | 24 |
| LOB 4 | 76 | 166 | 242 |
| LOB 5 | 27 | 6 | 33 |
| LOB 6 | 0 | 56 | 56 |
| LOB 7 | 0 | 0 | 0 |
| PXLOB 1 | 535 | 0 | 535 |
| PXLOB 2 | 175 | 158 | 333 |
| PXLOB 3 | 4 | 16 | 20 |
| PXLOB 4 | 100 | 237 | 337 |
| PXLOB 5 | 0 | 20 | 20 |
| PXLOB 6 | 11 | 0 | 11 |
| Grand Total | 1045 | 697 | 1742 |

*Letters refer to the original liquid medium tested (See Table III).

A sample of harvested embryos from four of the above lines (LOB 1, LOB 4, PXLOB 2 and PXLOB 4) were prepared for germination as follows: Stage 3 somatic embryos were transferred with forceps to small nylon disks and these disks were placed on the bottom surface of six empty wells of a 12-well plastic plate. The remaining six wells had previously been half-filled with sterile water. Typically, not more than 10 somatic embryos were placed in each empty well. The perimeter of the plate was sealed with PARAFILM and incubated for approximately 21 days in the dark at 25° C.

Partially dried somatic embryos were placed horizontally on the surface of MSG$_G$ medium. The medium was in 100×15 mm sterile plastic petri plates. Typically, about 10 somatic embryos were placed in each plate. The perimeter of plates were wrapped with PARAFILM. Plates with embryos were incubated in a growth chamber under a low light intensity at 25° C. until the embryos germinated (usually about 10 to 14 days). The embryos were germinated under fluorescent light with a 14-hour and 8-hour dark photoperiod at 25° C. Embryos that germinated elongated to approximately 1 to 2 cm and showed visible emergence of the radicle (root) to 0.5 to 3 cm. A total of 400 somatic embryos from the 4 different lines were tested for germination via the above procedure. Germination percentages ranged from 16% to 58%, depending upon the line×treatment medium combination.

The term "conversion" includes the acclimatization process that in vitro derived germinating somatic embryos undergo in order to survive under ex vitro (nonaxenic) conditions, and subsequent continued growth under ex vitro conditions. Embryos that had germinated were prepared for conversion as follows: When the length of the roots reached about 2 to 3 cm in the petri plates, the germinating plantlets were removed from the plates and planted in a horticultural soilless potting mix consisting of 2:1:2 peat:perlite:vermiculite, containing 602 g/m$^3$ OSMOCOTE® fertilizer (18-6-12), 340 g/m$^3$ dolomitic lime and 78 g/m$^3$ MICROMAX® micronutrient mixture (manufactured by Sierra Chem. Co.). in Ray leach tubes (RAY LEACH "CONE-TAINERS"® #SSCUV manufactured by Stuewe & Sons, Inc.). The leach tubes were placed in a greenhouse mist chamber. The environmental conditions in the mist chamber are as follows: (1) Mist was applied for 6–10 seconds every 15–30 minutes from 6:00 a.m. to 6:30 p.m., and generally turned off from 6:30 p.m. to 6:00 a.m.; (2) Temperature was maintained at 26° to 31° C. during the day and at 18° to 20° C. at night; and (3) Ambient light was admitted through black polypropylene shade cloth (51% shade) covering the greenhouse. The photoperiod was maintained at 16 hours or greater and supplemental light from high pressure sodium bulbs and or incandescent bulbs was provided when necessary to maintain this photoperiod.

When the plantlets had grown to approximately 5 to 15 cm in height, trays containing the resulting somatic embryo plants in leach tubes were removed from the mist chamber and placed on an open bench in the greenhouse for at least two weeks for acclimatization. Subsequently, somatic embryo plants in leach tube trays were moved to a shadehouse (framed structure covered with black polypropylene shade cloth) for approximately two weeks, and then to ambient outdoor conditions for a further acclimatization. Somatic embryo plants in leach tubes were watered with reverse osmosis treated water as required both during the greenhouse, shadehouse, and outdoors acclimatization period.

Acclimatized somatic embryo plants were carefully removed from the leach tubes so that the potting mix remained attached to roots and were transplanted to a prepared field site. A sample of 40 germinated/converted embryos from the above study were planted in a field planting in the coastal plain of South Carolina. To date (100%) of the somatic embryo plants have survived and appear phenotypically normal relative to standard *Pinus taeda* and *Pinus rigida*×*P. taeda* seedlings. Thus we were able to successfully germinate, convert and field-plant somatic embryos developed from liquid embryogenic suspension cultures of *Pinus taeda* and *Pinus rigida*×*P. taeda* hybrids.

BIBLIOGRAPHY

Attree, S. M., D. I. Dunstan, and L. C. Fowke, Initiation of embryogenic callus and suspension cultures, and improved regeneration from protoplasts, of white spruce (*Picea glauca*). *Canadian Journal of Botany* 67:1790–1795, 1989.

Attree, S. M., T. E. Tautorus, D. I. Dunstan, and L. C. Fowke. Somatic embryo maturation, germination, and soil establishment of plants of black and white spruce (*Picea mariana* and *Picea glauca*). *Canadian Journal of Botany* 68:2583–2589, 1990.

Becwar, M. R., R. Nagmani, and S. R. Wann. Initiation of embryogenic cultures and somatic embryo development in loblolly pine (*Pinus taeda*). *Canadian Journal of Forest Research* 20:810–817, 1990.

Becwar, M. R., T. L. Noland, and S. R. Wann. A method for quantification of the level of somatic embryogenesis among Norway spruce callus lines. *Plant Cell Reports* 6:35–38, 1987.

Becwar, M. R., S. R. Wann, M. A. Johnson, S. A. Verhagen, R. P. Feirer, and R. Nagmani. Development and characterization of in vitro embryogenic systems in conifers. *Somatic Cell Genetics of Woody Plants* (p. 1–18), 1988.

de Touchet, B., Y. Duval, and C. Pannetier. Plant regeneration from embryogenic suspension cultures of oil palm (*Elaeis guineensis* Jacq.). *Plant Cell Reports* 10:529–532, 1991.

Durzan, D. J. and P. K. Gupta. Somatic embryogenesis and polyembryogenesis in Douglas fir cell suspension cultures. *Plant Science* 52:229–235, 1987.

Ebert, A. and H. F. Taylor. Assessment of the changes of 2,4-dichlorophenoxyacetic acid concentrations in plant tissue culture media in the presence of activated charcoal. *Plant Cell Tissue and Organ Culture* 20:165–172, 1990.

Ebert, A., F. Taylor, and J. Blake. Changes of 6-benzylaminopurine and 2,4-dichlorophenoxyacetic acid concentrations in plant tissue culture media in the presence of activated charcoal. *Plant Cell Tissue and Organ Culture* 33:157–162, 1993.

Finer, J. J., H. B. Kriebel, and M. R. Becwar. Initiation of embryogenic callus and suspension cultures of eastern white pine (*Pinus strobus* L.). *Plant Cell Reports* 8:203–206, 1989.

Grossnickle, S.C., D. R. Roberts, J. E. Major, R. S. Folk, F. B. Webster, and B.C. S. Sutton. Integration of somatic embryogenesis into operational forestry: Comparison of interior spruce emblings and seedlings during production of 1+0 stock. In: Proceedings, Intermountain Forest Nursery Association. Aug. 12– 16, 1991. Park City, Utah. USDA Forest Service, General Tech. Report RM-211. pp. 106–113, 1992.

Gupta, P. K. and D. J. Durzan. Shoot multiplication from mature trees of Douglas-fir (*Pseudotsuga menziesii*) and sugar pine (*Pinus lambertiana*). *Plant Cell Reports* 4:177–179, 1985.

Gupta, P. K. and D. J. Durzan. Biotechnology of somatic polyembryogenesis and plantlet regeneration in loblolly pine. *Bio/Technology* 5:147–151, 1987a.

Gupta, P. K. and D. J. Durzan. Somatic embryos from protoplasts of loblolly pine proembryonal cells. *Bio/Technology* 5:710–712, 1987b.

Gupta, P. K. and G. S. Pullman. Method for reproducing coniferous plants by somatic embryogenesis using abscisic acid and osmotic potential variation. U.S. Pat. No. 5,036,007—issued Jul. 30, 1991.

Gupta, P. K., S. V. Kendurkar, V. M. Kulkarni, M. V. Shirgurkar, and A. F. Mascarenhas. Somatic embryogenesis and plants from zygotic embryos of coconut (*Cocos nucifera* L.) in vitro. *Plant Cell Reports* 3:222–225, 1984.

Gupta, P. K., G. S. Pullman, R. Timmis, M. E. Kreitinger, W. C. Carlson, and D. E. Welty. Scale-up somatic embryogenesis of conifers for reforestation (Abstract). In: Proceedings, 3rd Inter. Assoc. of Plant Tissue Culture Canadian Workshop on Plant Tissue Culture and Genetic Engineering, Univ. of Guelph, Guelph, Ontario, Canada. Jun. 17–20, 1992.

Hakman, I. and S. von Arnold. Plantlet regeneration through somatic embryogenesis in *Picea abies* (Norway spruce). *Journal of Plant Physiology* 121:149–158, 1985.

Hakman, I. C. and S. von Arnold. Somatic embryogenesis and plant regeneration from suspension cultures of *Picea glauca* (White spruce). *Physiologia Plantarum* 72:579–587, 1988.

Hakman, I. and L. C. Fowke. An embryogenic cell suspension culture of *Picea glauca* (White spruce). *Plant Cell Reports* 6:20–22, 1987.

Hakman, I., L. C. Fowke, S. von Arnold, and T. Eriksson. The development of somatic embryos in tissue cultures initiated from immature embryos of *Picea abies* (Norway spruce). *Plant Science* 38:53–59, 1985.

Jain, S. M., N. Dong, and R. J. Newton. Somatic embryogenesis in slash pine (*Pinus elliottii*) from immature embryos cultured in vitro. *Plant Science* 65:233–241, 1989.

Kermode, A. R. and J. D. Bewley. The role of maturation drying in the transition from seed development to germination. *Journal of Experimental Botany* 36:1906–1915, 1985.

Laine, E., P. Bade, and A. David. Recovery of plants from cryopreserved embryogenic cell suspensions of *Pinus caribaea*. *Plant Cell Reports* 11:295–298, 1992.

Laine, E. and A. David. Somatic embryogenesis in immature embryos and protoplasts of *Pinus caribaea*. *Plant Science* 69:215–224, 1990.

Michler, C. H., T. M. Voelker, and R. Moioffer. Effects of embryo explant type and developmental maturity on eastern white pine (*Pinus strobus L.*) embryogenic callus initiation (Abstract). In: Applications of biotechnology to tree culture, protection and utilization. (eds Haissig et al.) Columbus, Ohio. Aug. 5–8, 1991. USDA Forest Serv., Northeastern Forest Experiment Station, p. 117, 1991.

Preston, R. J. North American Trees, 4th edition. Iowa State Univ. Press, Ames. pp. 4–7, 1989.

Pullman, G. S. and P. K. Gupta. Method for reproducing coniferous plants by somatic embryogenesis using adsorbent materials in the development stage media. U.S. Pat. No. 5,034,326—issued Jul. 23, 1991.

Roberts, D. R. Process for the production, desiccation and germination of conifer somatic embryos. U.S. Pat. No. 5,183,757—issued Feb. 2, 1993.

Roberts, D. R., B. S. Flinn, D. T. Webb, F. B. Webster, and B. C. Sutton. Abscisic acid and indole-3-butyric acid regulation of maturation and accumulation of storage proteins in somatic embryos of interior spruce. *Physiologia Plantarum;* 78:355–360, 1990a.

Roberts, D. R., B. C. S. Sutton, and B. S. Flinn. Synchronous and high frequency germination of interior spruce somatic embryos following partial drying at high relative humidity. *Canadian Journal of Botany* 68:1086–1090, 1990b.

Sharma, D. R., S. Deepak, and J. B. Chowdhury. Regeneration of plantlets from somatic tissues of the date palm *Phoenix dactylifera* Linn. *Indian Journal of Experimental Biology* 24:763–766, 1986.

Tautorus, T. E., S. M. Attree, L. C. Fowke, and D. I. Dunstan. Somatic embryogenesis from immature and mature zygotic embryos, and embryo regeneration from protoplasts in black spruce (*Picea mariana* Mill.). *Plant Science* 67:115–124, 1990.

Tautorus, T. E., L. C. Fowke, and D. I. Dunstan. Somatic embryogenesis in conifers. *Canadian Journal of Botany* 69:1873–1899, 1991.

Tautorus, T. E., M. M. Lulsdorf, S. I. Kikcio, and D. I. Dunstan. Bioreactor culture of *Picea mariana* Mill. (black spruce) and the species complex *Picea glauca-engelmannii* (interior spruce) somatic embryos. Growth parameters. *Applied Microbiology and Biotechnology* 38:46–51, 1992.

Uddin, M. Somatic embryogenesis in gymnosperms. U.S. Pat. No. 5,187,092—issued Feb. 16, 1993.

von Arnold, S. and I. Hakman. Regulation of somatic embryo development in *Picea abies* by abscisic acid (ABA). *Journal of Plant Physiology* 132:164–169, 1988.

Webster, F. B., D. R. Roberts, S. M. McInnis, and B. C. S. Sutton. Propagation of interior spruce by somatic embryogenesis. *Canadian Journal of Forest Research* 20:1759–1765, 1990.

What is claimed is:

1. An improved method for establishing embryogenic liquid suspension cultures for use in somatic embryogenesis processes involving plants selected from the group consisting of *Pinus taeda, Pinus serotina, Pinus palustris, Pinus elliottii, Pinus rigida,* and hybrids thereof, which comprises:

(a) placing a suitable explant selected from the group consisting of immature zygotic embryos and megagametophytes containing immature zygotic embryos on culture initiation medium containing a sufficient amount of nutrients, 0.1 to 5.0 mg/l of auxin, 0.1 to 1.0 mg/l of cytokinin, 5.0 to 100.0 g/l of a sugar selected from the group consisting of glucose, maltose, sucrose, melezitose, and combinations thereof, and a level of gelling agent selected from the group consisting of 2.5 to 4.5 g/l of agar, 0.5 to 1.5 g/l of gellan gum, 3.0 to 5.0 g/l of agarose, and 1.5 to 3.0 g/l of AGARGEL, for 2 to 14 weeks under suitable environmental conditions to grow a culture containing embryogenic tissue; and (b) wherein the improvement comprises transferring the embryogenic tissue culture to liquid suspension culture maintenance medium containing a sufficient amount of nutrients, 0.1 to 100.0 mg/l of auxin, 0.05 to 10.0 mg/l of cytokinin, 5.0 to 100.0 g/l of a sugar selected from the group consisting of glucose, maltose, sucrose, melezitose, and combinations thereof, and about 0.1–10.0 g/l of activated carbon, for a sufficient time under suitable environmental conditions to establish a liquid embryogenic cell culture.

2. The method of claim 1 wherein said Pinus interspecies hybrid plant is selected from the group consisting of *Pinus rigida×Pinus taeda, Pinus taeda×Pinus rigida, Pinus serotina×Pinus taeda,* and *Pinus taeda×Pinus serotina.*

3. The method of claim 1 wherein the amount of activated carbon contained in the liquid suspension culture maintenance medium is about 0.5–5.0 g/l.

4. The method of claim 1 wherein said liquid suspension culture maintenance medium contains about 1.0 to 30.0 mg/l of auxin.

5. The method of claim 1 wherein said liquid suspension culture maintenance medium contains about 3.0 to 10.0 mg/l of auxin.

6. The method of claim 1 wherein said liquid suspension culture maintenance medium contains about 0.1 to 5.0 g/l of cytokinin.

7. The method of claim 1 wherein said liquid suspension culture maintenance medium contains about 0.5 to 3.0 g/l of cytokinin.

8. The method of claim 1 wherein the embryogenic tissue in the liquid suspension culture maintenance medium is cultured in a dark environment.

9. The method of claim 1 wherein the embryogenic tissue is transferred to semi-solid maintenance medium containing a sufficient amount of nutrients and plant growth hormones under suitable environmental conditions to maintain the embryogenic tissues, prior to transferring the embryogenic tissue to liquid suspension culture maintenance medium.

10. The method of claim 1 wherein the liquid embryogenic cell culture is subcultured.

11. The method of claim 1 wherein the embryogenic tissue culture has been cryopreserved.

12. The method of claim 1 wherein the liquid embryogenic cell culture is cryopreserved.

13. An improved method for reproducing plants selected from the group consisting of *Pinus taeda, Pinus serotina, Pinus palustris, Pinus elliottii, Pinus rigida,* and hybrids thereof, by somatic embryogenesis which comprises:

(a) placing a suitable explant selected from the group consisting of immature zygotic embryos and megagametophytes containing immature zygotic embryos on culture initiation medium containing a sufficient amount of nutrients, 0.1 to 5.0 mg/l of auxin, 0.1 to 1.0 mg/l of cytokinin, 5.0 to 100.0 g/l of a sugar selected from the group consisting of glucose, maltose, sucrose, melezitose, and combinations thereof, and a level of gelling agent selected from the group consisting of 2.5 to 4.5 g/l of agar, 0.5 to 1.5 g/l of gellan gum, 3.0 to 5.0 g/l of agarose, and 1.5 to 3.0 g/l of AGARGEL, for 2 to 14 weeks under suitable environmental conditions to grow a culture containing embryogenic tissue;

(b) wherein the improvement comprises transferring the embryogenic tissue culture to liquid suspension culture maintenance medium containing a sufficient amount of nutrients, 0.1 to 100.0 mg/l of auxin, 0.05 to 10.0 mg/l of cytokinin, 5.0 to 100.0 g/l of a sugar selected from the group consisting of glucose, maltose, sucrose, melezitose, and combinations thereof, and about 0.1–10.0 g/l of activated carbon, for a sufficient time under suitable environmental conditions to develop a liquid embryogenic cell culture;

(c) transferring at least 30 mg of the liquid embryogenic cell culture to embryo development medium containing a sufficient amount of nutrients, 5.0 to 250.0 mg/l of abscisic acid, a level of gelling agent selected from the group consisting of 6.0 to 12.0 g/l of agar, 1.75 to 4.00 g/l of gellan gum, 6.0 to 8.0 g/l of agarose, and 3.5 to 6.0 g/l of AGARGEL, and 20.0 to 70.0 g/l of a sugar selected from the group consisting of glucose, maltose, sucrose, and combinations thereof, for a sufficient time under suitable environmental conditions to develop stage 3 somatic embryos;

(d) separating the stage 3 somatic embryos from the development medium and partially drying the embryos by exposing the embryos to an atmosphere having a high relative humidity for sufficient time to permit the embryos to lose about 25% to 75% of their pre-dried weight;

(e) transferring the partially dried somatic embryos to germination medium containing a sufficient amount of nutrients, up to 10.0 g/l of activated carbon, a level of gelling agent selected from the group consisting of 6.0 to 9.0 g/l of agar, 1.75 to 3.50 g/l of gellan gum, 6.0 to 8.0 g/l of agarose, and 3.5 to 5.0 g/l of AGARGEL, and 20.0 to 40.0 g/l of a sugar selected from the group consisting of glucose, maltose, sucrose, and combinations thereof for a sufficient time under suitable environmental conditions to germinate the partially dried embryos;

(f) converting the germinated embryos into acclimatized plants; and (g) field planting the acclimatized plants.

14. The method of claim 13 wherein said Pinus interspecies hybrid plant is selected from the group consisting of *Pinus rigida*×*Pinus taeda, Pinus taeda*×*Pinus rigida, Pinus serotina*×*Pinus taeda,* and *Pinus taeda*×*Pinus serotina.*

15. The method of claim 13 wherein the amount of activated carbon contained in the liquid suspension culture maintenance medium is about 0.5–5.0 g/l.

16. The method of claim 13 wherein said liquid suspension culture maintenance medium contains about 1.0 to 30.0 mg/l of auxin.

17. The method of claim 13 wherein said liquid suspension culture maintenance medium contains about 3.0 to 10.0 mg/l of auxin.

18. The method of claim 13 wherein said liquid suspension culture maintenance medium contains about 0.1 to 5.0 g/l of cytokinin.

19. The method of claim 13 wherein said liquid suspension culture maintenance medium contains about 0.5 to 3.0 g/l of cytokinin.

20. The method of claim 13 wherein the embryogenic tissue in the liquid suspension culture maintenance medium is cultured in a dark environment.

21. The method of claim 13 wherein the embryogenic tissue is transferred to semi-solid maintenance medium containing a sufficient amount of nutrients and plant growth hormones under suitable environmental conditions to maintain the embryogenic tissues, prior to transferring the embryogenic tissue to liquid suspension culture maintenance medium.

22. The method of claim 13 wherein the liquid embryogenic cell culture is subcultured.

23. The method of claim 13 wherein the embryogenic tissue culture has been cryopreserved.

24. The method of claim 13 wherein the liquid embryogenic cell culture is cryopreserved.

25. The method of claim 13 wherein about 100 mg of the liquid embryogenic culture cells are placed on embryo development medium.

26. The method of claim 13 wherein the liquid embryogenic culture cells are transferred onto a sterile permeable membrane which has been placed on the surface of the embryo development medium.

* * * * *